United States Patent [19]

Wilson

[11] 4,181,360
[45] Jan. 1, 1980

[54] CUTTING FORCE SENSOR

[75] Inventor: Raymond G. Wilson, Tamworth, England

[73] Assignee: Coal Industry (Patents) Limited, London, England

[21] Appl. No.: 403,219

[22] Filed: Oct. 3, 1973

[30] Foreign Application Priority Data

Oct. 10, 1972 [GB] United Kingdom ............... 46570/72

[51] Int. Cl.² ........................................... E21C 39/00
[52] U.S. Cl. .................................... 299/1; 340/189 M
[58] Field of Search ............................. 299/1; 175/50; 340/189 M

[56] References Cited

U.S. PATENT DOCUMENTS

| | | | |
|---|---|---|---|
| 2,741,468 | 4/1956 | Alspaugh | 299/1 |
| 2,790,968 | 4/1957 | Cook et al. | 299/1 |
| 3,062,043 | 11/1962 | Marsh et al. | 340/189 M |
| 3,102,718 | 9/1963 | Eberle | 299/1 |
| 3,232,668 | 2/1966 | Moon | 299/1 |
| 3,350,944 | 11/1967 | DeMichele | 340/189 M |
| 3,550,959 | 12/1970 | Alford | 299/1 |
| 3,591,235 | 7/1971 | Addison | 299/1 |
| 3,594,587 | 7/1971 | Martens et al. | 340/189 M |

*Primary Examiner*—William Pate, III
*Attorney, Agent, or Firm*—James C. Wray

[57] ABSTRACT

A rotary cutter head of a mineral mining machine has a sensor to detect the cutting horizon of the cutter head relative to a boundary of a mineral seam and to derive a signal indicative of changes in the cutting horizon. The derived signal is fed to a radio transmitter on the cutter head which transmits a representative signal.

9 Claims, 3 Drawing Figures

CUTTING FORCE SENSOR

This invention relates to cutting sensors and in particular, although not exclusively, to cutting horizon sensors for use on rotary cutting heads of mineral mining machines.

It is known for a cutter tool to be held in a holder resiliently mounted on the rotary cutter head of a mineral mining machine and to provide means sensitive to the movement of the holder relative to the head to produce a signal indicative of said movement. With such a cutting head the signal derived from the means varies according to the cutting force acting on the tool and this in turn depends upon the type of mineral momentarily being cut by the tool and upon the tool penetration into the mineral. The signal is transmitted from the means which are mounted on the rotary cutter head to control means which are mounted on the body of the mining machine and which control the machine's steering mechanism in response to the signal to ensure the cutting horizon of the cutter head is kept within the boundary of the mineral seam. Thus with the known cutting heads the signal is fed through a coupling mechanism one half of which is rotary and the other half of which is non-rotary. Such coupling mechanisms have the disadvantage that they tend to be expensive and complicated and usually require the mining machine to be specially adapted to receive the coupling mechanism.

It is an object of the present invention to provide an improved cutting horizon sensor which overcomes or reduces the above mentioned disadvantages.

According to the present invention a cutting sensor for mounting on a cutting head having at least one cutter tool, comprises sensor means mountable on the cutting head for sensing a cutting condition of the cutter head and deriving a signal indicative of changes in the cutting condition and a radio transmitter mountable on the cutter head for transmitting a radio signal representative of the said signal.

Preferably, the cutting sensor is mounted on a cutting head of a mineral mining machine which in use traverses along a working face in a mineral seam, the sensor means being adapted to sense the cutting horizon of the cutter head relative to a boundary of the mineral seam, the derived signal being indicative of changes in the cutting horizon.

Preferably, the cutting sensor comprises radio receiver means remote from the cutter head for receiving the transmitted radio signal and instrumentation means electrically interconnected to the radio receiver and adapted to derive a further signal representative of the received radio signal.

The sensor means may be mounted on the cutter tool.

Alternatively, the sensor means may be mounted on a cutter tool holder.

As a further alternative, the sensor means may be mounted directly on the cutter head.

Preferably, the sensor means comprises a cutting force sensor which senses the cutting force acting on the cutter tool and which derives a signal indicative of changes in the cutting force.

Preferably, the sensor means comprises a load cell.

Alternatively, the sensor means may comprise nucleonic detector means for sensing electro magnetic radiation. Conveniently, the sensor means may comprise nucleonic emitter means.

The sensor means may detect variations in temperature of adjacent strata.

Advantageously, the radio transmitter is provided with aerial means which is encased within a body at least one face of which constitutes a radio window.

The invention also includes a machine having a cutting sensor and an associated radio transmitter.

By way of example only, one embodiment of the present invention will be described with reference to the accompanying drawings in which.

Figure 1:
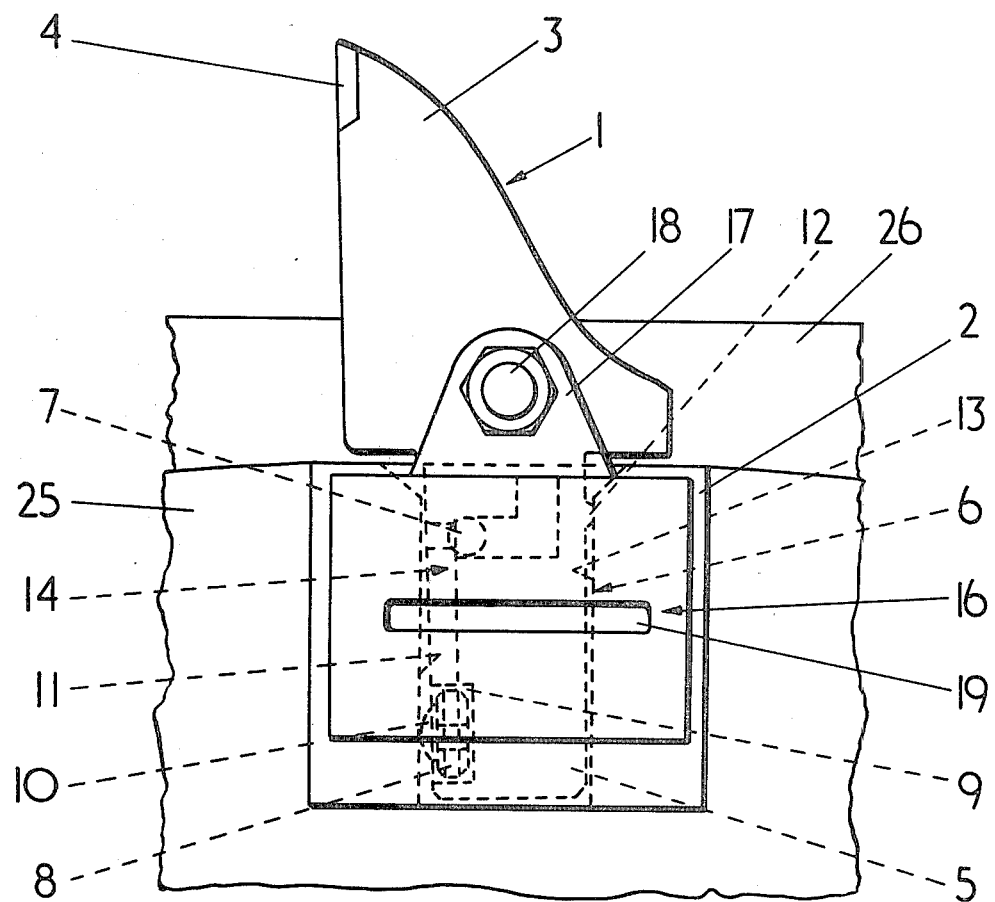
FIG. 1 is a side view of a cutter unit provided with a cutting force sensor constructed in accordance with the present invention.
Figure 2:
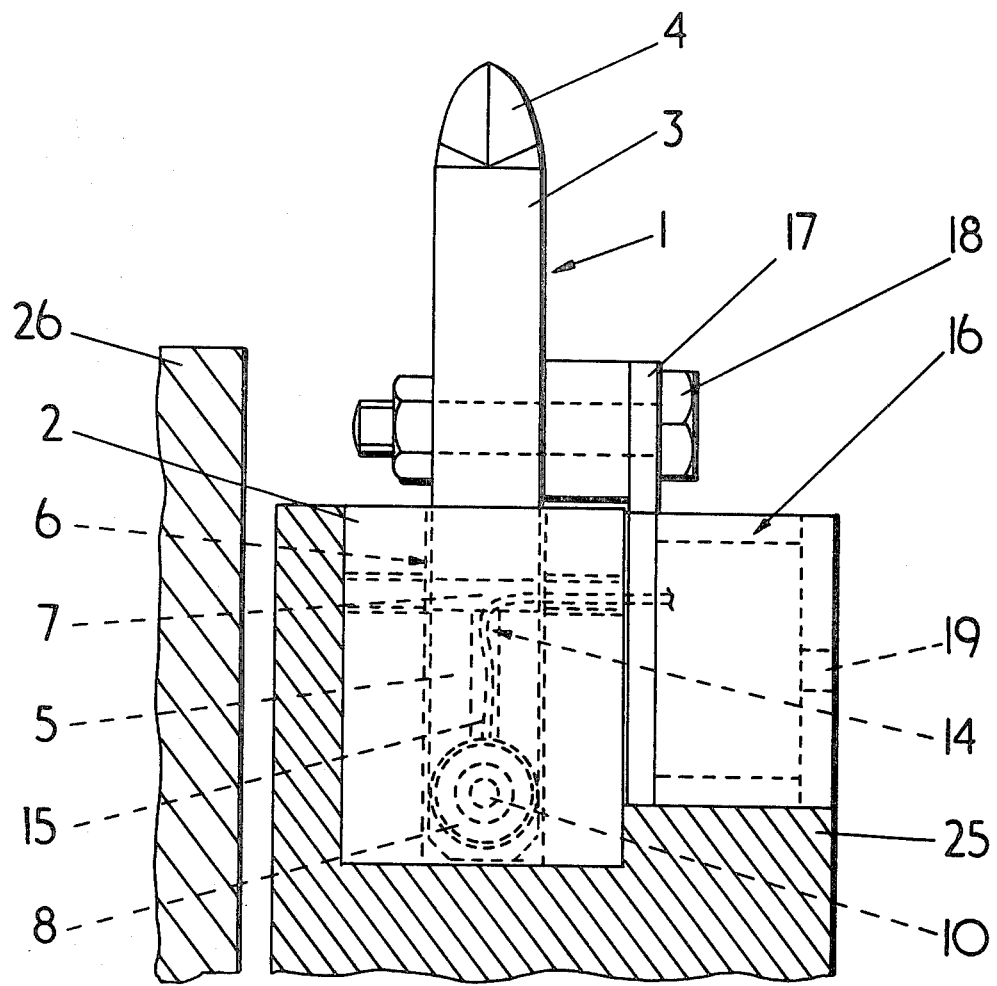
FIG. 2 is an incomplete front view of FIG. 1.

Referring to the drawings, FIGS. 1 and 2 show a cutter unit comprising a mineral cutter tool 1 releasably mounted in a cutter tool holder 2 which in use is welded adjacent the periphery of a rotary cutter head 25 of a longwall face coal mining machine 26 (only parts of the cutter head and of the mining machine being shown in FIG. 1). The cutter tool 1 has a body 3 provided with a cutting tip 4 and a shank 5 which engages in a through passage 6 formed in the cutter tool holder 2, the shank being retained in the passage by a cross pin 7 resiliently mounted in the shank and the ends of which releasably engage in "L"-shaped slots provided in the walls of the cutter tool holder.

In operation the machine traverses to and fro along the face with the rotary cutting head winning coal which is loaded onto a face conveyor extending along the path of the machine. As the cutting head rotates the cutter tool 1 cuts through bands of mineral having differing cutting characteristics. Consequently, during cutting the cutting force acting on the cutter tool varies, for example, if the cutter tool cuts through a hard rock band formed within the coal seam the cutting force associated with the cutter tool passing through the band is higher than when the cutter tool is passing through bands of relatively soft coal on each side of the rock. By continuously sensing the cutting force on the cutter tool and picking out the peak associated with the rock band it is possible to steer the cutter head so that its cutting horizon lies within the seam. The machine's steering mechanism is controlled so that the peak associated with the rock band is kept within a preselected range of the cutting head's cutting profile.

In alternative installations the rock of differing hardness which is selected as the datum may be at or adjacent to the roof boundary or the floor boundary of the mineral seam.

The cutting force acting on the cutter tool 1 is sensed by sensor means constituted by a load cell 8 which is housed within a recess 9 formed within the leading face of the cutter tool shank 5 and which has a spherical load button 10 arranged to abut the leading wall 11 of the passage 6. The rear face of the shank 5 has a small projection 12 which abuts the rear wall 13 of the passage 6 and about which the cutter tool 1 pivots thus ensuring that during cutting the button 10 is always in contact with the wall 11.

The shank 5 is also formed with a slot 14 within which are housed leads 15 electrically interconnecting the load cell 8 to a box member 16 which houses electronic equipment to be described later in this specification with reference to FIG. 3. The box member 16 is secured to a support bracket 17 which is connected to the body 3 of the cutter tool 1 by a cross bolt 18. One wall of the box member 16 is provided with a radio window 19 which contains a radio aerial encased within a hard plastics material which allows the unattenuated propogation of radio waves.

Figure 3:
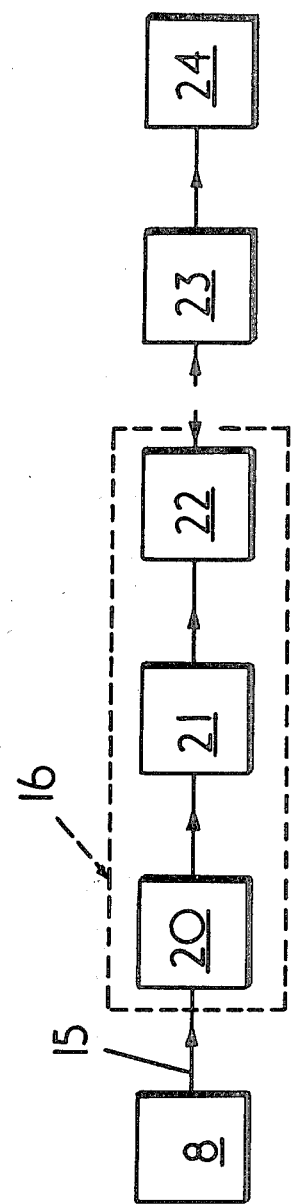
FIG. 3 is a block electrical circuit diagram for the cutting force sensor.

FIG. 3 shows a block circuit diagram of the cutting force sensor including the load cell 8 and the electronic equipment housed within the box member 16. This electronic equipment comprises an electronic amplifier 20 arranged to receive the signal from the load cell 8 via the leads 15, a voltage/frequency converter 21 arranged to convert the voltage of the amplifier signal to a frequency modulated signal which is fed to a radio transmitter 22 also housed within the box member 16 which transmits radio signal representative of the received frequency modulated signal.

The transmitted radio signal is picked up by a radio receiver 23 which is remote from the cutting head and which feeds a frequency modulated signal representative of the received radio signal to instrumentation means 24 as for example an electromagnetic tape recorder or a chart recorder or control means arranged to control the machine's steering mechanism and arranged to steer the cutting head so that its cutting horizon is kept within the mineral seam.

In some installations a de-modulator instrument may be provided to convert the frequency modulated signal.

In operation, the cutter tool 1 is inserted in any selected cutter tool holder 2 on the cutter head. As soon as cutting starts a transient signal representative of the cutting force acting on the cutter tool is fed from the load cell 8 via the amplifier 20 and voltage/frequency converter 21 to the radio transmitter 22 which transmits a representative radio signal. The transmitted signal is picked up by the radio receiver 23 which feeds a signal representative of the received signal to the recorder or control means 24.

If a recorder is used the information is collected and later analysed to form part of a preliminary survey to see if the mineral seam might lend itself to being worked by machines provided with cutting force sensors.

Alternatively, the signal may be fed to steering control means which control the machine's cutting horizon.

From the above description it can be seen that the present invention provides a cutting force sensor for use on a rotary cutting head of a mineral mining machine which is simple and which can be applied to most mining machines without requiring modification of the machine.

In other modifications of the invention the load cell is fitted within the wall of the cutter tool holder. This embodiment permits a conventional cutter tool to be used which facilitates easy replacement of the tool when it becomes worn or damaged.

In still further modifications of the invention the cutter tool holder is resiliently mounted and the sensor means detects movements of the cutter tool holder during cutting.

In other embodiments of the invention the sensor means may comprise nucleonic detector means which detects electromagnetic radiation from the strata adjacent to the cutter head. The electro-magnetic radiation may be the natural radiation from the strata as it may arise from nucleonic emitter means provided by the sensor means.

In still further embodiments of the invention the sensor means detects variations in temperature in the mineral seam relative to adjacent strata.

I claim:

1. The mineral cutting machine sensing apparatus comprising a cutter head mounted for rotation on a machine, a pocket in the cutter head, a cutter having a shank mounted in the pocket on the cutter head, the cutter having a cutter blade mounted at a distal forward end of the cutter pivot means mounted on the cutter transverse to the cutter at a medial portion of the cutter, and wherein the compressible botton is mounted between a front wall of the pocket and a proximal frontal portion of the cutter shank for compressing the botton as cutting force rearward on the cutter blade pivots the cutter about the pivot means, a sensor in the compressible button member for producing electrical signals upon relative movement of the cutter shank and the pocket, wires connected to the sensor, and a radio transmitter mounted on the cutter head and connected to the wires for accepting the electrical signals from the sensor and transmitting radio signals representative of the electrical signals.

2. The mineral cutter machine apparatus of claim 1 further comprising pin means extending through the cutter means intermediate the pivot means and proximal end and wherein the wires pass into the cutter shank and through a cavity in the cutter shank, through a cavity in the pin, and axially outward from the pin into the transmitter, which is mounted laterally outside the pocket.

3. The mineral cutter machine apparatus of claim 1 further comprising a box mounted on the cutting head adjacent the pocket, and wherein the transmitter is mounted in the box and wherein one wall of the box includes an antenna window.

4. A machine having a cutting sensor as claimed in claim 1, for mounting on a cutter head of a mineral mining machine which in use traverses along a working face in a mineral seam, the sensor means being adapted to sense the cutting horizon of the cutter head relative to a boundary of the mineral seam, the derived signal being indicative of changes in the cutting horizon.

5. A machine having a cutting sensor as claimed in claim 4, comprising radio receiver means remote from the cutter head for receiving the radio signal and instrumentation means electrically interconnected to the radio receiver and adapted to derive a further signal representative of the received radio signal.

6. A machine having a cutting sensor as claimed in claim 5, in which the sensor means is mounted on the cutter tool.

7. A machine having a cutting sensor as claimed in claim 5, further comprising a cutter tool holder mounted on the cutting head, in which the sensor means is mounted on the cutter tool holder.

8. A machine having a cutting sensor as claimed in claim 5, in which the sensor means is mounted directly on the cutter head.

9. A machine having a cutting sensor as claimed in claim 4 in which the radio transmitter is encased within a body at least a portion of one face of which constitutes a radio window.

* * * * *